United States Patent [19]

Sirrenberg et al.

[11] 4,002,744
[45] Jan. 11, 1977

[54] 0-ETHYL-0-ISO-BUTYL-0-(2,2-DICHLOROVINYL)-THIONO-PHOSPHORIC ACID ESTER

[75] Inventors: Wilhelm Sirrenberg, Sprockhovel; Bernhard Homeyer, Opladen, both of Germany

[73] Assignee: Bayer Aktiengesellschaft, Leverkusen, Germany

[22] Filed: Apr. 9, 1975

[21] Appl. No.: 566,647

[30] Foreign Application Priority Data

Apr. 24, 1974 Germany .......................... 2419624

[52] U.S. Cl. ................................ 424/219; 260/957
[51] Int. Cl.² ...................... A01N 9/36; C07F 9/165
[58] Field of Search ................... 260/957; 424/219

[56] References Cited

UNITED STATES PATENTS 3,745,198   7/1973   Soloway et al. ................... 260/957

Primary Examiner—Anton H. Sutto
Attorney, Agent, or Firm—Burgess, Dinklage & Sprung

[57] ABSTRACT

0-Ethyl-0-iso-butyl-0-(2,2-dichlorovinyl)thionophosphoric acid ester of the formula

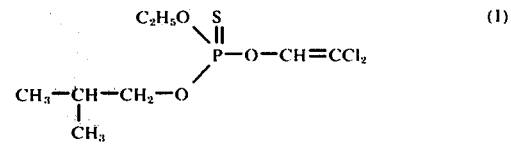

which possesses insecticidal properties.

3 Claims, No Drawings

O-ETHYL-O-ISO-BUTYL-O-(2,2-DICHLOROVINYL)-THIONO-PHOSPHORIC ACID ESTER

The present invention relates to and has for its objects the provision of O-ethyl-O-iso-butyl-O-(2,2-dichlorovinyl)-thionophosphoric acid ester which possesses insecticidal properties, active compositions in the form of mixtures of such compound with solid and liquid dispersible carrier vehicles, and methods for producing such compound and for using such compound in a new way especially for combating pests, e.g. insects, with other and further objects becoming apparent from a study of the within specification and accompanying examples.

It is known from German Published Specification DOS No. 2,150,108 that O,O-dimethyl-O-(2,2-dichlorovinyl)-thionophosphoric acid ester (Compound A) possesses insecticidal properties.

The present invention provides O-ethyl-O-iso-butyl-O-(2,2-dichlorovinyl)-thionophosphoric acid ester of the formula

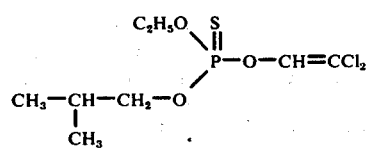

Surprisingly, the O-ethyl-O-iso-butyl-O-(2,2-dichlorovinyl)-thionophosphoric acid ester (I) according to the invention exhibits a better insecticidal, above all soil-insecticidal, activity, coupled with a very good long-term action, than the previously known O,O-dimethyl-O-(2,2-dichlorovinyl)-thionophosphoric acid ester of analogous structure and of the same type of action. Accordingly, the compound according to the invention represents a genuine enrichment of the art.

This compound has been found to have an excellent insecticidal action.

The invention also provides a process for the production of O-ethyl-O-iso-butyl-O-(2,2-dichlorovinyl)-thionophosphoric acid ester of the formula (I) in which an O-(2,2-dichlorovinyl)-thionophosphoric acid ester dihalide of the formula

in which

Hal is halogen atom (preferably chlorine is reacted with iso-butanol and with ethanol, in either order.

If the first reaction is with iso-butanol, then an intermediate may be formed having the formula

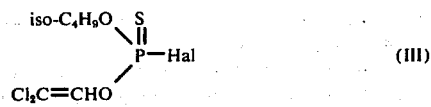

in which

Hal has the abovementioned meaning.

The reactions may be carried out in the presence of an acid acceptor. The alcohol may be in the form of an alcoholate.

If the starting materials used are O-(2,2-dichlorovinyl)-thinonophosphoric acid ester dichloride and iso-butanol in the first reaction stage and sodium ethylate in the second reaction stage, the course of the reaction can be represented by the following formula scheme:

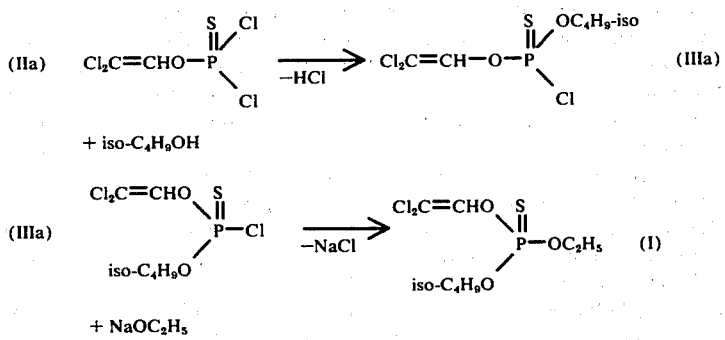

The O-(2,2-dichlorovinyl)-thionophosphoric acid ester dihalide of formula (II) can be prepared according to processes described in the literature, even on a large industrial scale.

The reactions according to the invention are preferably carried out in the presence of a solvent or diluent. Practically all inert organic solvents can be used for this purpose. These include, in particular, aliphatic and aromatic (optionally chlorinated) hydrocarbons, for example benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, for example acetonitrile and propionitrile.

Alternatively, an excess of the alcoholic reactants can also serve as the solvent, if desired.

All customary acid-binding agents can be used as acid acceptors for example in the reaction with the ethanol. Alkali metal carbonates and alkali metal alcoholates, such as sodium carbonate and potassium carbonate, sodium ethylate and potassium ethylate, have proved particularly successful, as have aliphatic, aromatic or heterocyclic amines, for example triethylamine and trimethylamine, dimethylaniline, dimethylbenzylamine and pyridine.

The reaction temperature can be varied within a substantial range. In general, the reaction is carried out at −20° to 100°, preferably at −10° to 40° C.

To carry out the process, the alcoholic component is generally added dropwise to the thionophosphoric acid dihalide (II), it being possible to choose either isobutanol followed by ethanol, or the converse sequence, as desired. The reaction is preferably carried out in the presence of one of the abovementioned solvents, and if appropriate in the presence of an acid acceptor, at the stated temperatures.

After completion of the first reaction stage, any excess alcohol which may serve as a reactant and at the same time as the solvent, may be distilled off and the residue taken up in methylene chloride and worked up in the usual manner, while in the second reaction stage, after completion of the reaction, the reaction mixture may be poured into ice water. After separation of the phases, the organic phase may be worked up in the usual manner by washing, drying, evaporation of the solvent and, if appropriate, distillation of the residue.

The new compound of formula (I) is obtained as an oil, can be purified by distillation and is characterised by its refractive index.

As already mentioned, the O-ethyl-O-iso-butyl-O-(2,2-dichlorovinyl)-thionophosphoric acid ester according to the invention is distinguished by an excellent insecticidal, above all soil-insecticidal, activity. The persistent long-term action should also be singled out. The substance is not only active against soil insects and leaf insects but also against hygiene pests and pests of stored products.

For this reason, the compound according to the invention can be employed successfully as a pesticide in plant protection and in the hygiene field and the field of protection of stored products.

To the sucking insects there belong, in the main, aphids (Aphidae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus Korschelti*), the rosy apple aphid (*Sappaphis mali*), the mealy plum aphid (*Hyalopterus arundinis*) and the cherry blackfly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*); the assassin bug (Rhodnius prolixus) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (Lepidoptera) such as the diamond-back moth (*Plutella maculipennis*), the gypsy moth (*Lymantria dispar*), the brown-tail moth (*Euproctis chrysorrhoea*), and tent caterpillar (*Malacosoma neustria*); further, the cabbage moth (*Mamestra brassicae*) and the cut-worm (*Agrotis segetum*), the large white butterfly (*Pieris brassicae*), the small winter moth (*Cheimatobia brumata*), the green oak tortrix moth (*Tortrix viridana*), the fall army-worm (*Laphygma frugiperda*) and cotton worm (*Prodenia litura*), the ermine moth (Hyponomeuta padella), the Mediterranean flour moth (*Ephestia kühniella*) and greater wax moth (*Galleria mellonella*).

Also to be classed with the biting insects are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beelte (*Byturus tomentosus*), the bean weevil (*Bruchidius* = *Acanthoscelides obtectus*), the leather beetle (Dermestes frischi), the khapra beetle (*Trogoderma granarium*), the flour beetle (*Tribolium castaneum*), the northern corn billbug (*Calandra* or *Sitrophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (Agriotes spec.) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia aegina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and ester thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, or nematocides, acaricides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects, which comprises applying to at least one of correspondingly (a) such insects, and (b) the corresponding habitat thereof, i.e. the locus to be protected, e.g. to a growing crop, to an area where a crop is to be grown or to a domestic animal, a correspondingly combative or toxic amount, i.e. an insecticidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Duration of action/soil insects

Test insect: *Phorbia brassicae*

Solvent: 3 parts by weight of acetone

Emulsifier: 1 part by weight of alkylaryl glycol ether

To produce a suitable preparation of active compound, 1 part by weight of active compound was mixed with the stated amount of solvent, the stated amount of emulsifier was added and the concentrate was diluted with water to the desired concentration.

The active compound preparation was intimately mixed with the soil. The concentration of the active compound in the preparation was practically immaterial, the only decisive factor being the amount by weight of active compound per unit volume of soil, which is quoted in ppm (mg of active compound per liter of soil). The treated soil was filled into 5 liter Mitscherlich pots and these pots were allowed to stand at room temperature while constantly being kept moist. At intervals of 2 weeks, 250 cc samples of soil were taken and infested with test insects. The degree of destruction of the insects, in 1 %, was determined after 48 hours. The taking of samples was continued until the active compound mixed with the soil destroyed less than 90% of the insects. The duration of action of the compound was deduced from this decrease in action, and is quoted in weeks.

The active compounds, amounts used and results can be seen from Table 1 which follows:

Table 1

(Duration of action in the soil, for the case of *Phorbia brassicae* grubs)
(Active compound concentration: 10 ppm)

| Active compound | Degree of destruction in % after weeks | | | | | | |
|---|---|---|---|---|---|---|---|
| | 1 | 2 | 4 | 8 | 12 | 16 | 18 |
| $\begin{array}{c} CH_3O \\ \phantom{CH_3O}\diagdown \\ \phantom{CH_3O}\phantom{x}P-OCH=CCl_2 \\ \phantom{CH_3O}\diagup \\ CH_3O \end{array}$ (known) (A) | 95 | 0 | | | | | |
| $\begin{array}{c} CH_3 \\ \phantom{CH_3}\diagdown \\ \phantom{xx}CH-CH_2-O \\ \phantom{CH_3}\diagup \phantom{xxxxxxxx}\diagdown \\ CH_3 \phantom{xxxxxxxxx} P-OCH=CCl_2 \\ \phantom{xxxxxxx}\diagup \\ \phantom{xxxxx}C_2H_5O \end{array}$ (I) | 100 | 100 | 100 | 100 | 100 | 100 | 95 |

EXAMPLE 2

Critical concentration test/soil insects

Test insect: *Tenebrio molitor* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration. The preparation of active compound was intimately mixed with the soil. The concentration of the active compound in the preparation was practically immaterial, the only decisive factor being the amount by weight of active compound per unit volume of soil, which is quoted in ppm (for example mg/1). The soil was filled into pots and the pots were left to stand at room temperature. After 24 hours the test insects were introduced into the treated soil and after a further 48 hours the degree of effectiveness of the active compound was determined in % by counting the dead and live test insects. The degree of effectiveness was 100% if all test insects had been killed and was 0% if exactly as many test insects were still alive as in the case of the control.

The active compounds, amounts used and results can be seen from the Table 2 which follows:

EXAMPLE 3

Critical concentration test/soil insects

Test insect: *Agrotis segetum* caterpillars in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration. The preparation of active compound was intimately mixed with the soil. The concentration of the active compound in the preparation was practically immaterial, the only decisive factor being the amount by weight of active compound per unit volume of soil, which is quoted in ppm (for example mg/1). The soil was filled into pots and the pots were left to stand at room temperature. After 24 hours the test insects were introduced into the treated soil and after a further 48 hours the degree of effectiveness of the active compound was determined in % by counting the dead and live test insects. The degree of effectiveness was 100% if all test insects had been killed and was 0% if exactly as many test insects were still alive as in the case of the control.

The active compounds, the amounts used and results can be seen from the table 3 which follows:

Table 2

(*Tenebrio molitor* larvae in the soil)
Degree of destruction in % at an active compound concentration of

| Active compound | 20 | 10 | 5 | 2.5 | 1.25 | 0.625 | ppm |
|---|---|---|---|---|---|---|---|
| $\begin{array}{c} CH_3O \\ \phantom{CH_3O}\diagdown \\ \phantom{CH_3O}\phantom{x}P-OCH=CCl_2 \\ \phantom{CH_3O}\diagup \\ CH_3O \end{array}$ (known) (A) | 100 | 100 | 50 | 30 | 0 | | |
| $\begin{array}{c} CH_3 \\ \phantom{CH_3}\diagdown \\ \phantom{xx}CH-CH_2-O \\ \phantom{CH_3}\diagup \phantom{xxxxxxxx}\diagdown \\ CH_3 \phantom{xxxxxxxxx} P-OCH=CCl_2 \\ \phantom{xxxxxxx}\diagup \\ \phantom{xxxxx}C_2H_5O \end{array}$ (I) | 100 | 100 | 100 | 100 | 80 | 50 | |

Table 3

| Active compound | (Agrotis segetum caterpillars in the soil) Degree of destruction in % at an active compound concentration of | | | | | |
|---|---|---|---|---|---|---|
| | 20 | 10 | 5 | 2.5 | 1.25 | ppm |
| $\begin{array}{c}CH_3O\\ \phantom{CH_3O}\diagdown\overset{S}{\underset{\phantom{|}}{\|}}\\ \phantom{CH_3O}\phantom{\diagdown}P\text{---}OCH\text{=}CCl_2\\ CH_3O\diagup\\ \text{(known) (A)}\end{array}$ | 100 | 100 | 50 | 0 | | |
| $\begin{array}{c}CH_3\\ \phantom{CH_3}\diagdown\\ \phantom{CH_3}\phantom{\diagdown}CH\text{---}CH_2\text{---}O\diagdown\overset{S}{\underset{\phantom{|}}{\|}}\\ CH_3\diagup\phantom{CH\text{---}CH_2\text{---}O}\diagdown\\ \phantom{CH_3\diagup CH\text{---}CH_2\text{---}O\phantom{\diagdown}}P\text{---}OCH\text{=}CCl_2\\ \phantom{CH_3\diagup CH\text{---}CH_2\text{---}}C_2H_5O\diagup\\ \phantom{CH_3\diagup CH\text{---}CH_2\text{---}C_2H_5O}(I)\end{array}$ | 100 | 100 | 100 | 100 | 50 | |

EXAMPLE 4

First stage

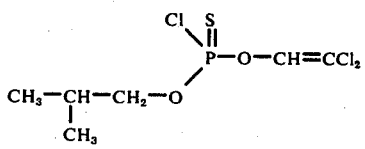

100 cm³ of iso-butanol were added dropwise to 61.5 g (0.25 mole) of O-(2,2-dichlorovinyl)-trionophosphoric acid ester dichloride at 0° C. The batch was then stirred for 1 hour at 0° C and a further 4 to 6 hours at 20° C, the excess iso-butanol was thereafter distilled off under reduced pressure, the residue was taken up in methylene chloride and the remaining iso-butanol was washed out with water. After drying the organic phase over sodium sulfate, the solvent was removed under reduced pressure. 70 g (98.5% of theory) of O-iso-butyl-O-(2,2-dichlorovinyl)-thionophosphoric acid di-ester chloride remained as an oil. The substance was sufficiently pure for further reactions. It could be distilled if required and then boiled at 102° to 106° C/0.01 mm Hg. The distilled product had a refractive index of $N_D^{20} = 1.5018$.

Second stage

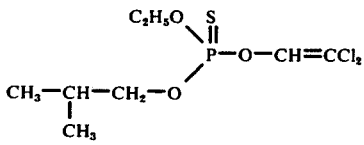 (I)

An ethanol solution containing 34 g (0.5 mole) of sodium ethylate was added dropwise at −10° C to a solution of 141.8 g (0.5 mole) of the O-iso-butyl-O-(2,2-dichlorovinyl)-thionophosphoric acid ester chloride, prepared in the first stage as described above, in 800 cm³ of toluene. The batch was stirred for half hour at −10° C and then for a further 3 hours at 20° C and was then poured into 1 liter of ice water. The phases were separated and the organic layer was washed twice more with half liter of ice water at a time. After drying the organic phase, the solvent was distilled off under reduced pressure and the residue was distilled. The product boiled at 94–100° C/0.01 mm Hg. 86 g (58.5% of theory) of O-ethyl-O-iso-butyl-O-(2,2-dichlorovinyl)-thionophosphoric acid ester of refractive index $n_D^{20}$ : 1.4768 were obtained.

It will be appreciated that the instant specification and examples are set forth by way of illustration and not limitation, and that various modification and changes may be made without departing from the spirit and scope of the present invention.

What is claimed is:

1. O-Etyl-O-iso-butyl-O-(2,2-dichlorovinyl)-thionophosphoric acid ester of the formula

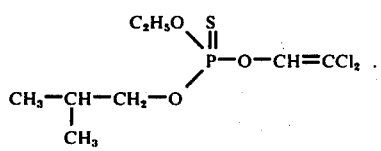

2. An insecticidal composition containing as active ingredient an insecticidally effective amount of a compound according to claim 1 in admixture with a diluent.

3. A method of combating insect pests which comprises applying to the pests or a habitat thereof an insecticidally effective amount of a compound according to claim 1.

* * * * *